United States Patent
Shi et al.

(10) Patent No.: US 11,680,947 B2
(45) Date of Patent: Jun. 20, 2023

(54) MARKER POLYPEPTIDE OF BOTHROPS ATROX-LIKE THROMBIN AND METHOD THEREOF FOR DETECTING SPECIES SOURCE AND CONTENT OF SNAKE VENOM-LIKE THROMBIN AND APPLICATION

(71) Applicants: Shandong Institute for Food and Drug Control, Shandong (CN); Penglai Nuokang Pharmaceutical Co., Ltd., Shandong (CN)

(72) Inventors: Feng Shi, Shandong (CN); Weijian Wang, Shandong (CN); Ruiqing Xian, Shandong (CN); Liping Gong, Shandong (CN); Congcong Wang, Shandong (CN); Baojian Hang, Shandong (CN); Jing Dong, Shandong (CN); Honghai Li, Shandong (CN)

(73) Assignees: Shandong Institute for Food and Drug Control, Shandong (CN); Penglai Nuokang Pharmaceutical Co., Ltd., Shandong (CN)

( * ) Notice: Subject to any disclaimer, the term of this patent is extended or adjusted under 35 U.S.C. 154(b) by 0 days.

(21) Appl. No.: 17/932,301

(22) Filed: Sep. 15, 2022

(65) Prior Publication Data

US 2023/0092234 A1 Mar. 23, 2023

(30) Foreign Application Priority Data

Sep. 15, 2021 (CN) .......................... 202111078334.7

(51) Int. Cl.
G01N 33/68 (2006.01)
G16C 20/20 (2019.01)

(52) U.S. Cl.
CPC ......... *G01N 33/6848* (2013.01); *G16C 20/20* (2019.02); *G01N 2333/4613* (2013.01); *G01N 2333/745* (2013.01); *G01N 2800/42* (2013.01)

(58) Field of Classification Search
CPC ....... G01N 33/6848; G01N 2333/4613; G01N 2333/745; G01N 2800/42; G16C 20/20
See application file for complete search history.

(56) References Cited

PUBLICATIONS

Bhat, Shreesha K., et al. "Serine proteinases from Bothrops snake venom activates PI3K/Akt mediated angiogenesis." Toxicon 124(2016): 63-72. (Year: 2016).*

* cited by examiner

*Primary Examiner* — Jennifer Wecker
*Assistant Examiner* — Michael Paul Shimek
(74) *Attorney, Agent, or Firm* — JCIPRNET

(57) ABSTRACT

Disclosed are specifically a marker polypeptide of a *Bothrops atrox*-like thrombin and a method thereof for detecting species source and content of a snake venom-like thrombin and an application, relating to the technical field of snake venom detection. An amino acid sequence of the marker polypeptide is EAYNGLPAK (SEQ ID NO:1), and the marker polypeptide may be used to detect the species source and content of the snake venom-like thrombin in a sample. The marker polypeptide of the present disclosure may play an important role in characterizing the species source and content of the snake venom-like thrombin in the sample, and fill in the blank of a quality standard of snake venom of the *Bothrops atrox*.

4 Claims, 9 Drawing Sheets

Specification includes a Sequence Listing.

MARKER POLYPEPTIDE OF BOTHROPS ATROX-LIKE THROMBIN AND METHOD THEREOF FOR DETECTING SPECIES SOURCE AND CONTENT OF SNAKE VENOM-LIKE THROMBIN AND APPLICATION

CROSS-REFERENCE TO RELATED APPLICATION

This application claims the priority benefit of China application no. 202111078334.7, filed on Sep. 15, 2021. The entirety of each of the above-mentioned patent application is hereby incorporated by reference herein and made a part of this specification.

BACKGROUND OF THE INVENTION

1. Technical Field

The present disclosure relates to the technical field of viper snake venom detection, in particular to a marker polypeptide of a *Bothrops atrox*-like thrombin and a method thereof for detecting species source and content of a snake venom-like thrombin and an application.

2. Background Art

Information disclosed in the background of the present disclosure is only for enhancement of understanding of the general background of the present disclosure, and should not necessarily be taken as an acknowledgement or any form of suggestion that this information forms the prior art already known to those of ordinary skill in the art.

Snake venom is liquid secreted by venomous snakes from venom glands, and contains a variety of proteins, mainly including a metalloproteinase, a phospholipase A2, a nerve growth factor, a thrombin-like enzyme, a serine protease, an L-amino acid oxidase and the like, and also containing some small molecular peptides, amino acids, carbohydrates, lipids, nucleosides, biogenic amines and metal ions and the like. The composition of the snake venom is very complex, and the toxicity, pharmacological and toxicological effects of the different snake venom have their own characteristics. The diversity of molecules in the snake venom determines the diversity of snake venom functions. A series of drugs with different biological functions such as hemostasis, thrombolysis, blood pressure, pain relief and anti-tumor are developed by using the snake venom as a raw material. Herein, snake venom hemocoagulase-like drugs are a class of hemostatic drugs with a snake venom-like thrombin as a main active ingredient, and it occupies an irreplaceable and important position in the field of hemostasis, accounting for nearly 50% of the market share of the hemostatic drugs.

A *Bothrops atrox*-like thrombin is a protease-like substance with a hemostatic effect extracted from the snake venom of *Bothrops atrox*, has the arginine esterase activity, and may play an important role in the blood coagulation process. It is mainly used in clinical treatment of hemorrhagic diseases, and may be used in various medical conditions that need to reduce bleeding or stop bleeding, for example: bleeding and hemorrhagic diseases in clinical departments such as internal medicine, surgery, obstetrics and gynecology, ophthalmology, otolaryngology, and stomatology; it may also be used to prevent bleeding, such as preoperative medication, which may avoid or reduce intraoperative and postoperative bleeding; and it may be used for adjuvant treatment of gastrointestinal bleeding, hemophilic hematoma, thrombocytopenic diseases with bleeding, and is more suitable for a bleeding patient who is ineffective with the traditional hemostatic drugs. At present, the launched snake venom hemocoagulase-like drugs mainly come from the *Bothrops atrox, Agkistrodon acutus, Viperarussellii* and *Agkistrodon halys ussuriensis*. Thrombin-like enzymes from the different snake species sources are different in structure, the mechanisms of action thereof are different, and there are also differences in the corresponding pharmacologic action. Therefore, the establishing of a method with strong specificity and high sensitivity to characterize its species source and content has extensive social benefits and economic effects for controlling the quality of a snake venom hemocoagulase-like product.

SUMMARY OF THE INVENTION

In view of the above problems, the present disclosure provides a marker polypeptide of a *Bothrops atrox*-like thrombin and a method thereof for detecting species source and content of a snake venom-like thrombin and an application, the marker polypeptide may play an important role in characterizing the species source and detection content of the snake venom-like thrombin in the sample, and fill in the blank of a quality standard of snake venom of the *Bothrops atrox*. Specifically, in order to achieve the above purpose, a technical scheme of the present disclosure is as follows:

In a first aspect of the present disclosure, a marker polypeptide of a *Bothrops atrox*-like thrombin is disclosed, and its amino acid sequence is EAYNGLPAK (SEQ ID NO: 1).

In a second aspect of the present disclosure, a method for detecting a species source of a snake venom-like thrombin is disclosed, and the following steps are used:

(1) adding a trypsin to a sample to be detected to perform enzymolysis pre-treatment, and taking a supernatant for future use;

(2) performing qualitative ion pair and quantitative ion pair detection on the supernatant; and (3) if a chromatogram obtained in the step (2) shows a chromatographic peak consistent with the retention time of a control marker polypeptide chromatogram, it is indicated that the sample to be detected is from *Bothrops atrox;* and otherwise, it is not a source of the *Bothrops atrox,* herein the amino acid sequence of the control marker polypeptide is EAYNGLPAK (SEQ ID NO: 1).

Further, in the step (1), the enzymolysis pre-treatment method includes: dissolving and diluting the sample to be detected with ammonium bicarbonate solution, then adding trypsin solution, and taking a supernatant after a reaction at a suitable temperature.

Further, in the step (2), the supernatant is injected into a liquid chromatography-mass spectrometer respectively, and an electrospray positive ion mode is used to perform multi-reaction monitoring.

Further, in the step (2), a mass-to-charge ratio m/z double-charge 481.9 to 315.2 is used as a quantitative ion pair, and 481.9 to 485.2 is used as a qualitative ion pair.

Further, in detection conditions of liquid phase and mass spectrometry in the liquid chromatography-mass spectrometer, the liquid phase conditions are: Thermo Hypersil GOLD C18 chromatographic column (100 mm×2.1 mm, 3 μm); column temperature: 40° C.; injection volume: 10 μL; flow rate: 0.3 mL/min; a mobile phase A is 0.1% formic acid solution, B is 0.1% formic acid acetonitrile, and gradient elution is performed, elution program: 0 to 2 min, mobile phase A 90%; 2 to 6 min, mobile phase A 90% to 60%; 6.1 to 8 min, mobile phase A 30%; and 8.1 to 10 min, mobile phase A 90%.

Further, in the detection conditions of the liquid phase and mass spectrometry in the liquid chromatography-mass spectrometer, the mass spectrometry conditions are: an electrospray ion source, a positive ion scanning mode, and multi-reaction monitoring; the vortex ion spray temperature is 500° C.; the ionization voltage is 5.5 kV; the collision chamber exit potential is 10 V; the entry potential (EP) is 10 V; the collision energy (CE) is 20 V, and the declustering potential (DP) is 80 V.

In a third aspect of the present disclosure, a method for detecting a species content of a snake venom-like thrombin is disclosed, including the following steps:

(i) taking the marker polypeptide of the *Bothrops atrox*-like thrombin of which the amino acid sequence is EAYN-GLPAK (SEQ ID NO: 1), dissolving and diluting to prepare series concentration reference substance solution;

(ii) using the above sample derived from the *Bothrops atrox* detected in the method for detecting the species source of the snake venom-like thrombin in the step (3) as an object to be detected, dissolving and diluting with ammonium bicarbonate solution, and then adding trypsin solution, taking a supernatant after a reaction at a suitable temperature, as test substance solution, injecting the test substance solution into a liquid chromatography-mass spectrometer, and using an electrospray positive ion mode to perform multi-reaction monitoring; and (iii) extracting the chromatogram of which the mass-to-charge ratio double-charge is 481.9 to 315.2, taking the concentration of the marker polypeptide in the series concentration reference substance solution in the step (i) as an abscissa, taking the peak area corresponding to the chromatogram in the step (ii) as an ordinate, calculating a linear regression equation, calculating the concentration of the test substance solution from the regression equation, and then calculating the thrombin-like content in the object to be detected.

Further, in the step (iii), r of the linear regression equation is >0.99.

In a fourth aspect of the present disclosure, an application of the method for detecting the species source and/or content of the snake venom-like thrombin in the fields of biology and medicine and the like is disclosed.

Compared with the prior art, the present disclosure has the following beneficial effects: because the thrombin-like amino acid sequences of the known snake species such as *Agkistrodon halys ussuriensis, Viperarussellii* and *Agkistrodon acutus* do not contain the marker polypeptide of the *Bothrops atrox*-like thrombin, the marker polypeptide may be used to detect the species source and content of the *Bothrops atrox*-like thrombin in the sample to be detected. In addition, the detection limit of the marker polypeptide of the *Bothrops atrox* venom may reach 0.5 ng/mL, the limit of quantification may reach 1.25 ng/mL, and the detection accuracy is high, which fills the blank of the quality standard of the *Bothrops atrox* venom, and may significantly improve the quality control level of the *Bothrops atrox* venom, to guarantee the efficacy and safety of *Bothrops atrox*-like thrombin products in clinical medication.

BRIEF DESCRIPTION OF THE DRAWINGS

Drawings of the description constituting a part of the present disclosure are used to provide further understanding of the present disclosure, and exemplary embodiments of the present disclosure and descriptions thereof are used to explain the present disclosure, and do not constitute improper limitation to the present disclosure. Hereinafter, implementation schemes of the present disclosure are described in detail with reference to the drawings, herein.

DETAILED DESCRIPTION OF THE EMBODIMENTS

In the following descriptions, specific details of the present disclosure are further described in order to provide thorough understanding of the present disclosure. Terms used in the description of the present disclosure are only used to describe the advantages and features of the present disclosure, and are not intended to limit the present disclosure.

Unless otherwise defined, all technical and scientific terms used in the present disclosure have the same meaning as understood by those skilled in the art which belongs to the technical field of the present disclosure. Unless otherwise specified, drugs or reagents used in the present disclosure are used in accordance with product instructions or by using conventional methods in the field. Technical schemes of the present disclosure are further described now according to the drawings and specific implementation modes of the description.

In the following embodiments, the screening and determination of the marker polypeptide of the *Bothrops atrox*-like thrombin of the present disclosure, instruments and devices used, chromatography and mass spectrometry conditions, mass spectrometry conditions and the like all adopt the content disclosed in Embodiment 1 in a patent document "marker polypeptide of snake venom-like thrombin of Agkistrodon halys ussuriensis and application thereof" (the application number is 202010752988.2).

First Embodiment

Preparation of solution for marker polypeptide screening includes the following steps:

5 mg of a *Bothrops atrox*-like thrombin is put into a volumetric flask with a volume of 10 mL, and then the *Bothrops atrox*-like thrombin is dissolved with ammonium bicarbonate solution with a molar concentration of 25 mmol/L and the volume is fixed to 10 mL, and 200 μL of solution is precisely measured, to obtain solution a.

10 μL of dithiothreitol solution with a concentration of 0.2 mol/L is added to the solution a, mixed uniformly, and reacted for 1 hour under a heating condition of a constant-temperature water bath at 60° C., and then 20 μL of iodoacetamide solution with a concentration of 0.2 mol/L is added, and it is protected from light for 30 min.

Then 760 μL of the ammonium bicarbonate solution with a concentration of 25 mmol/L and 10 μL of trypsin solution (newly prepared) with a concentration of 0.4 mg/mL are added, reacted at 37° C. for 90 min, inactivated at 90° C. for 10 min, cooled to a room temperature, and centrifuged at 1200 rpm for 10 min, a supernatant is taken as solution for marker peptide screening.

A nanoliter liquid phase is used to separate and inject a sample, and a high-resolution mass spectrometry is used to collect primary and secondary mass spectra of the solution for the marker peptide screening.

Figure 1:
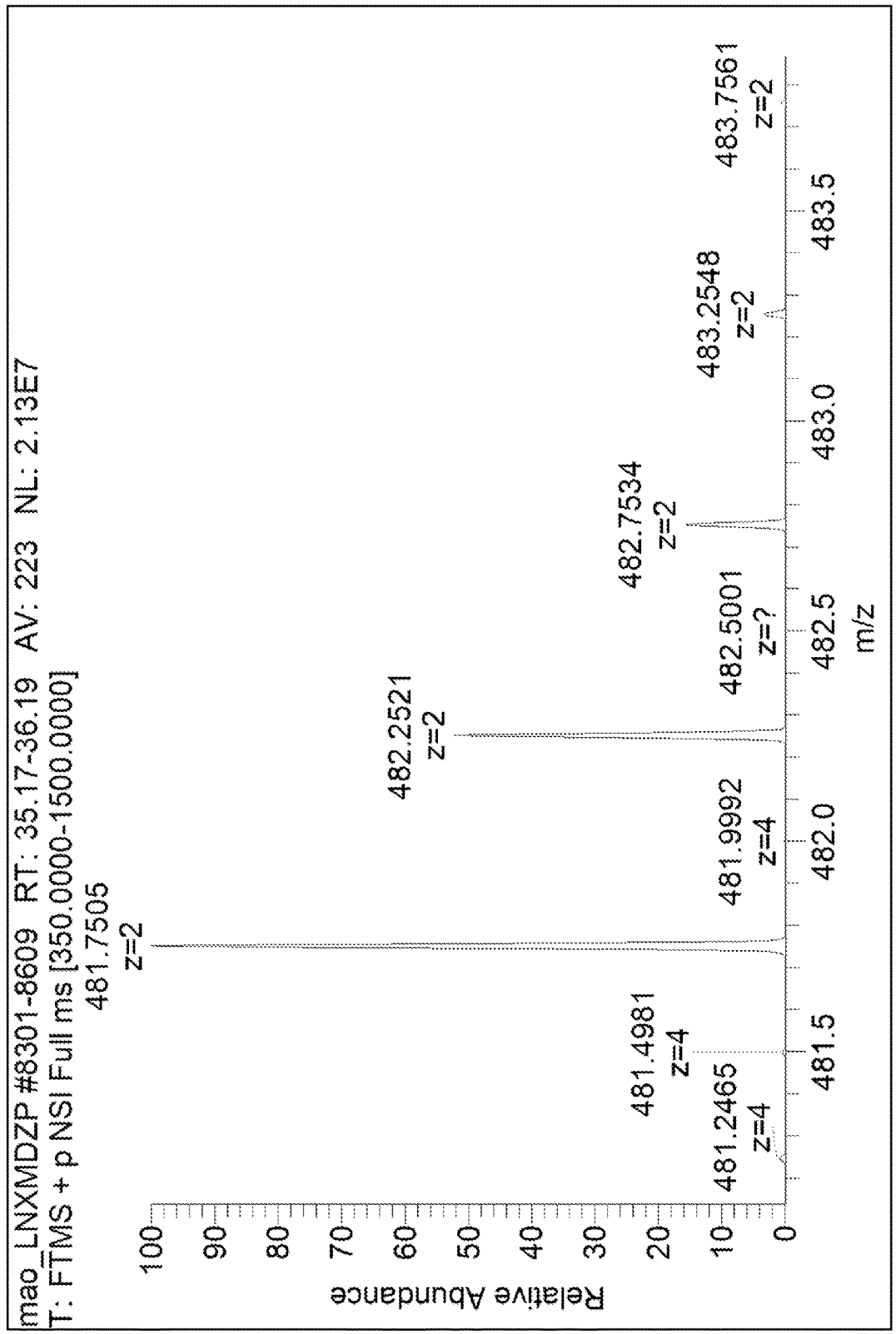
FIG. 1 is a primary mass spectrogram of a marker polypeptide of a *Bothrops atrox*-like thrombin screened out in Embodiment 1.
Figure 2:
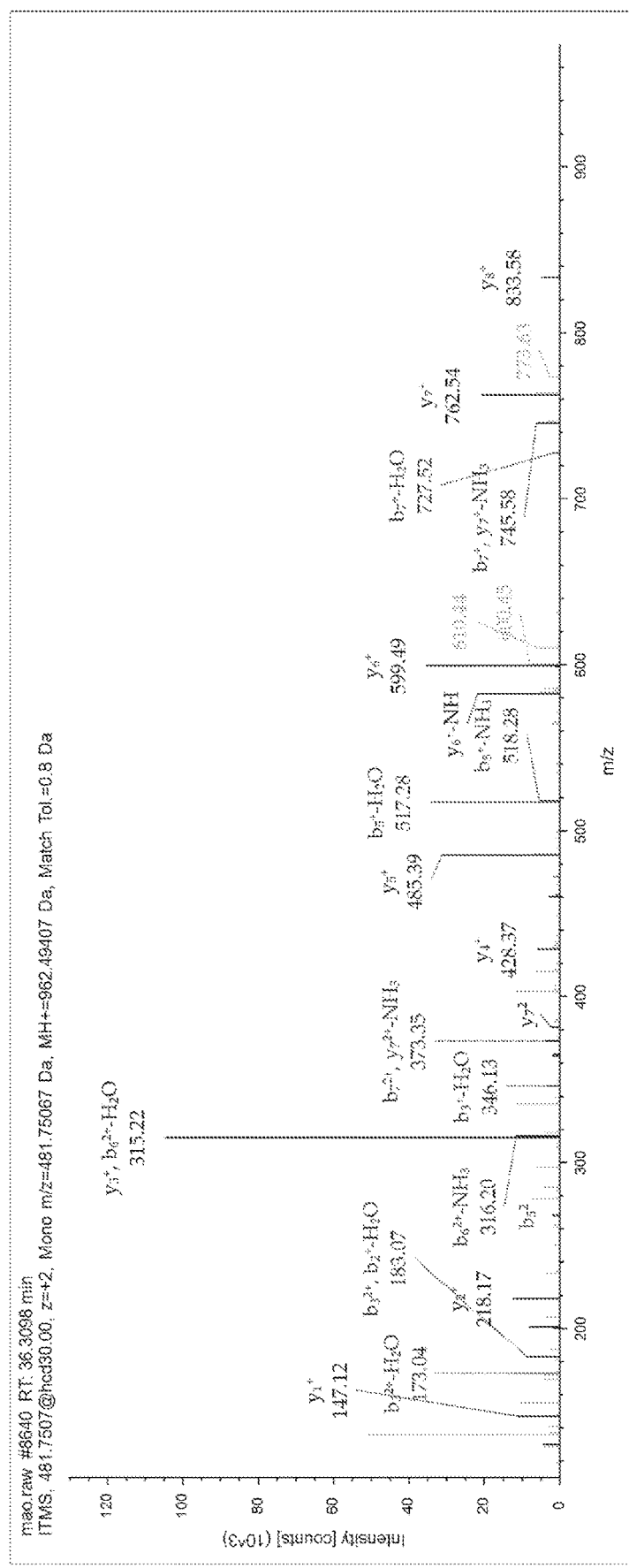
FIG. 2 is a secondary mass spectrogram of the marker polypeptide of the *Bothrops atrox*-like thrombin screened out in Embodiment 1.
Figure 3:
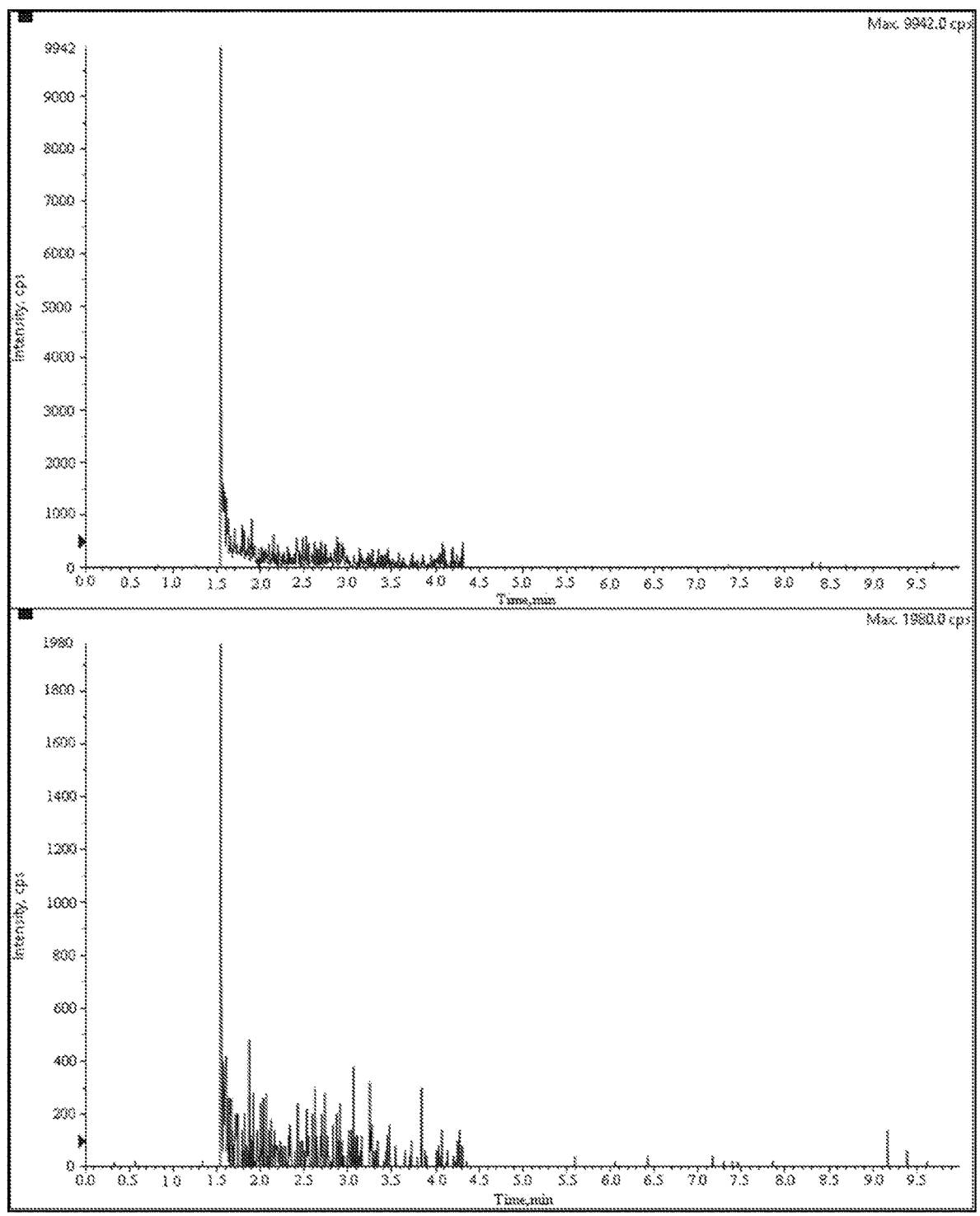
FIG. 3 is a specificity investigation spectrum of blank solution in Embodiment 2.
Figure 4:
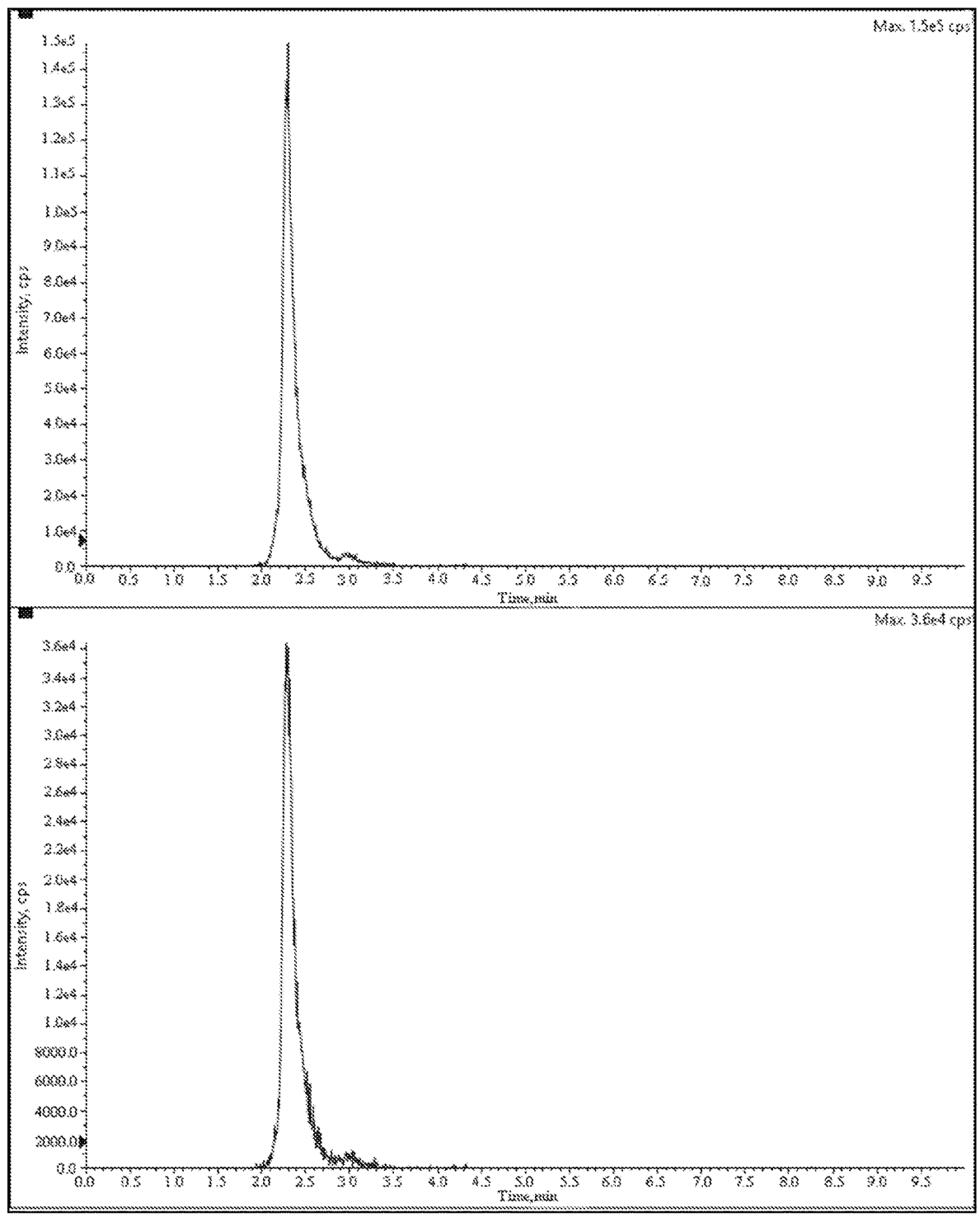
FIG. 4 is a specificity investigation spectrum of marker polypeptide control solution in Embodiment 2.
Figure 5:
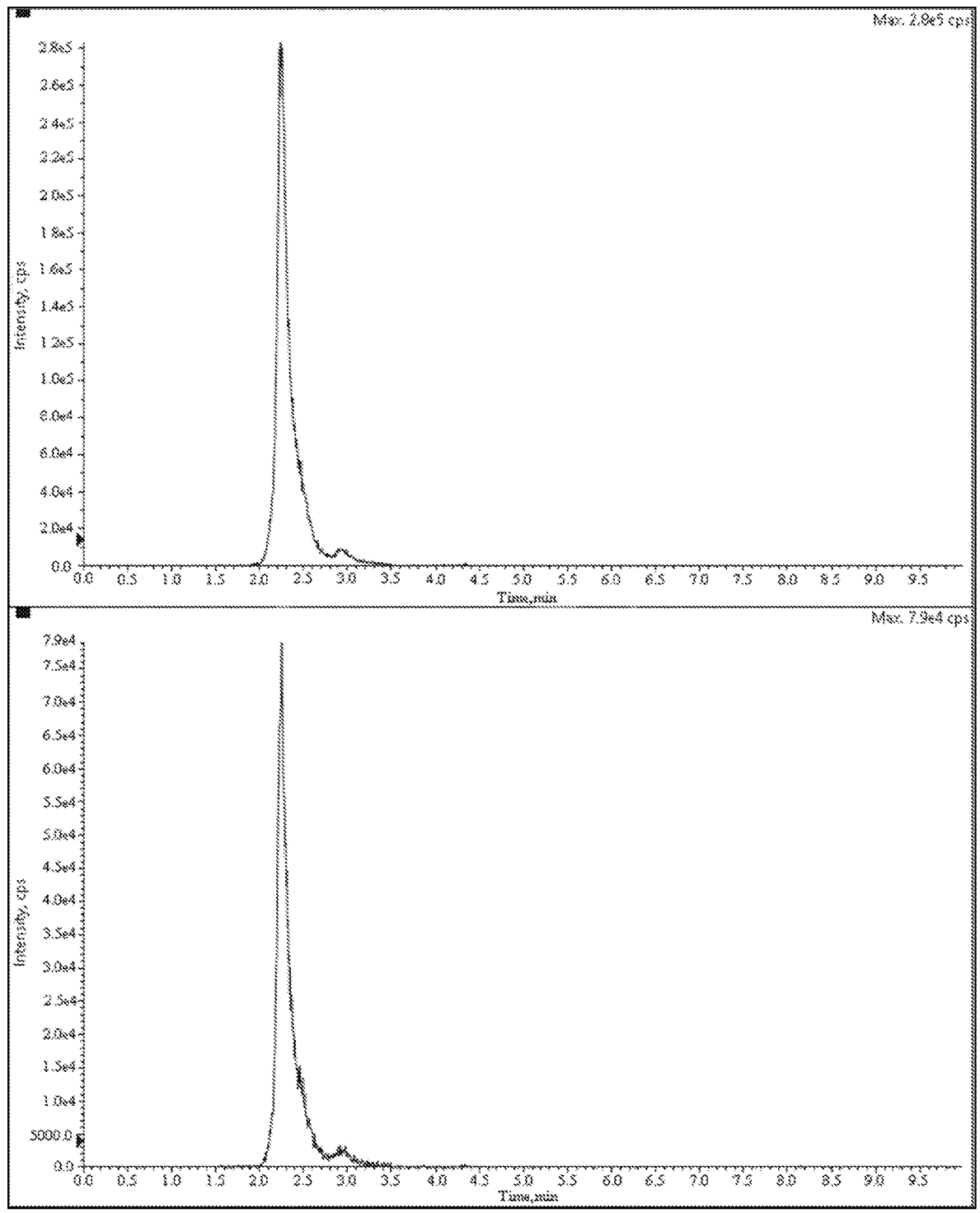
FIG. 5 is a specificity investigation spectrum of venom sample solution of *Bothrops atrox* in Embodiment 2.
Figure 6:
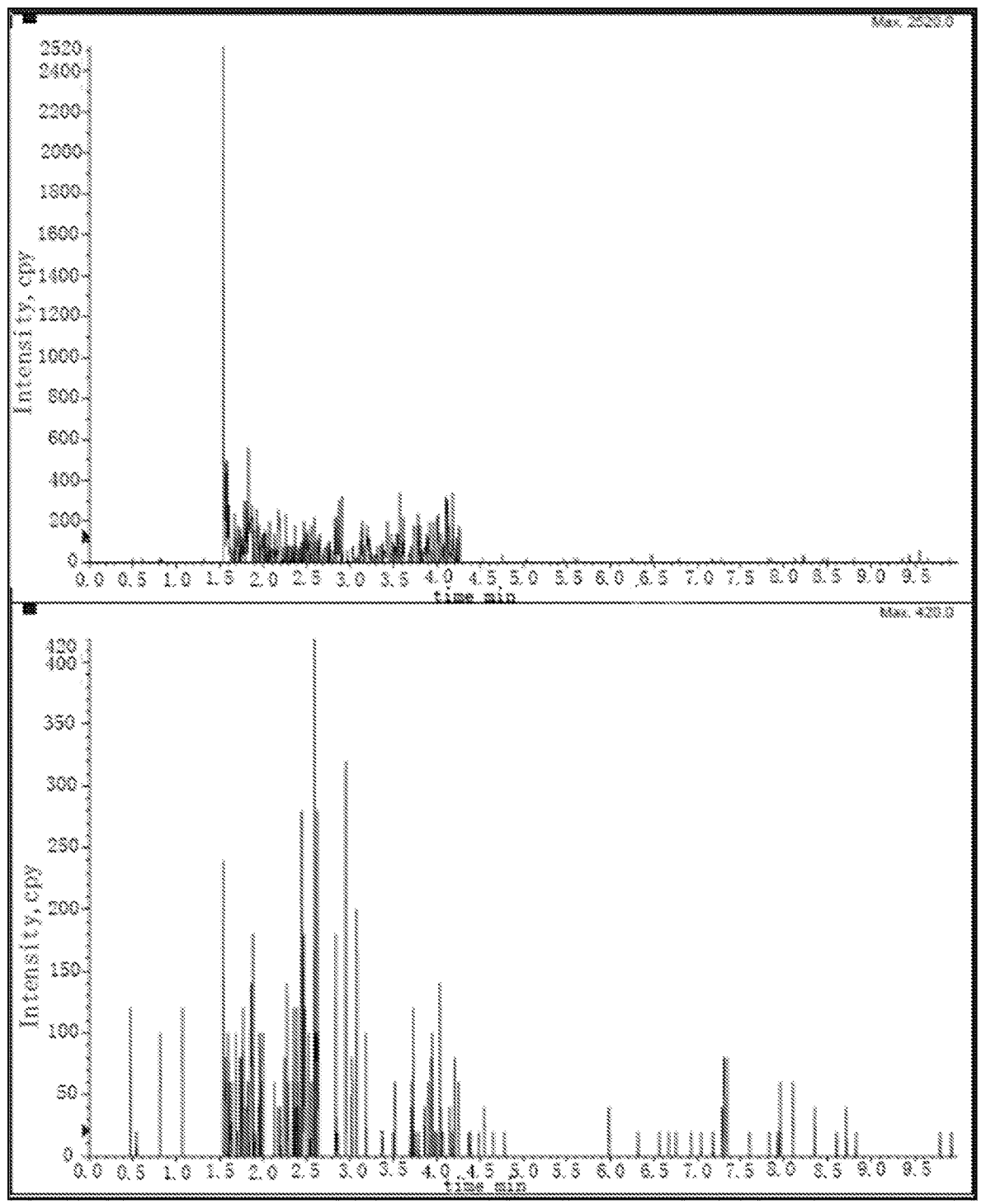
FIG. 6 is a specificity investigation spectrum of negative sample solution in Embodiment 2.
Figure 7:
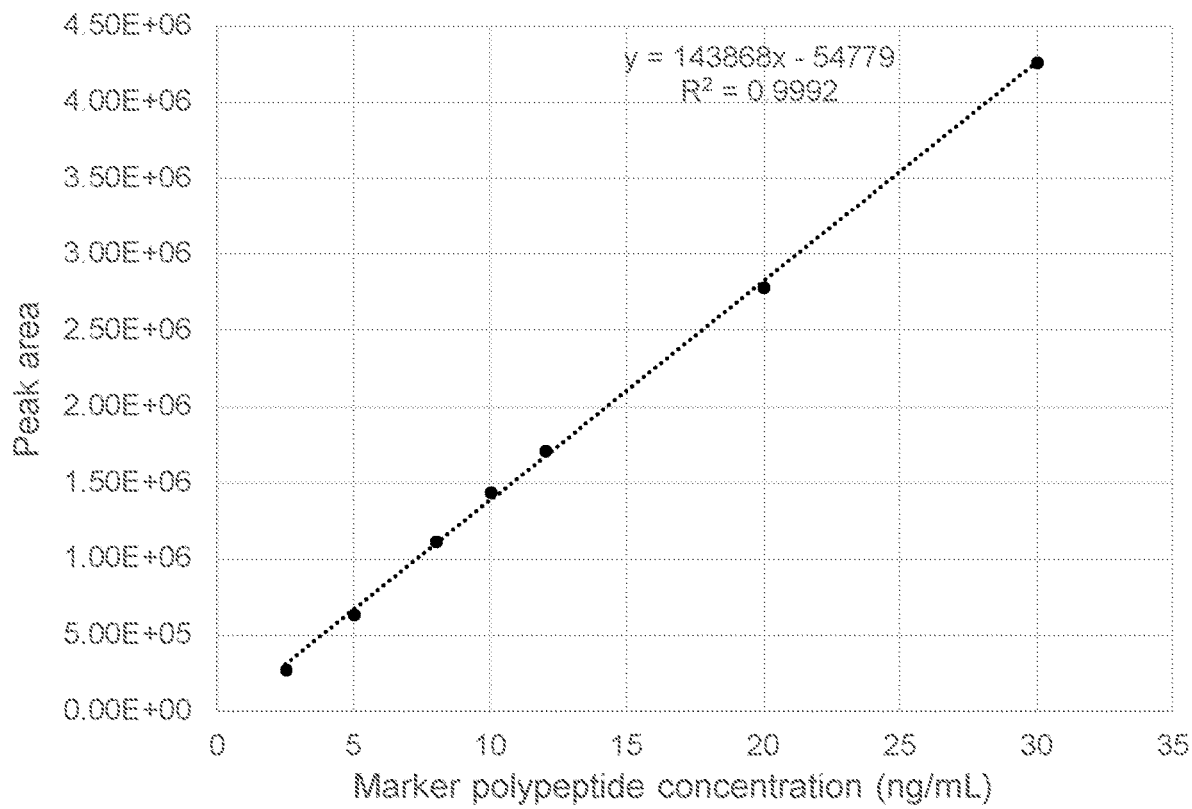
FIG. 7 is a linearity and range spectrum of the venom sample solution of the *Bothrops atrox* in Embodiment 2.
Figure 8:
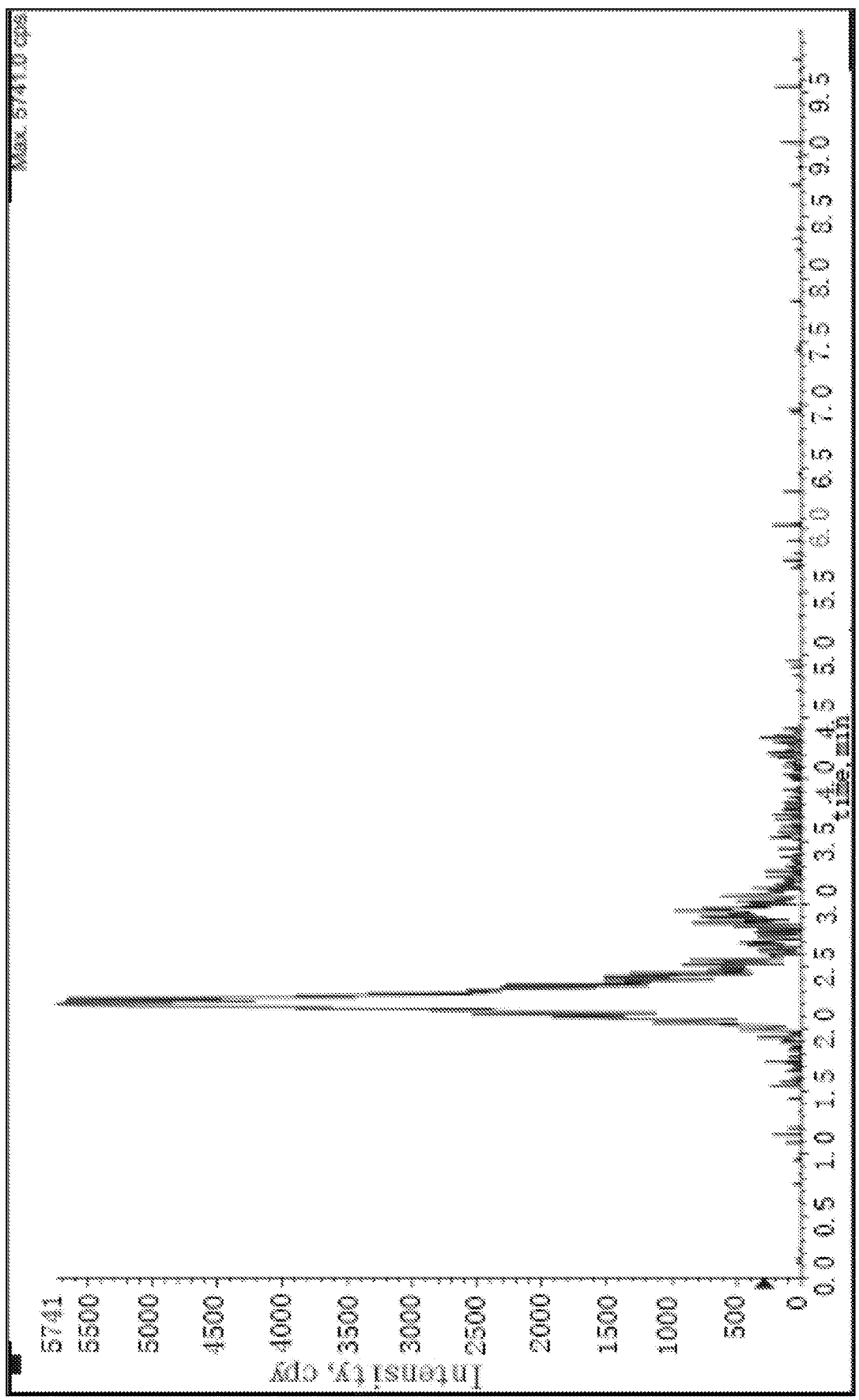
FIG. 8 is a detection limit spectrum of the venom sample solution of the *Bothrops atrox* in Embodiment 2.
Figure 9:
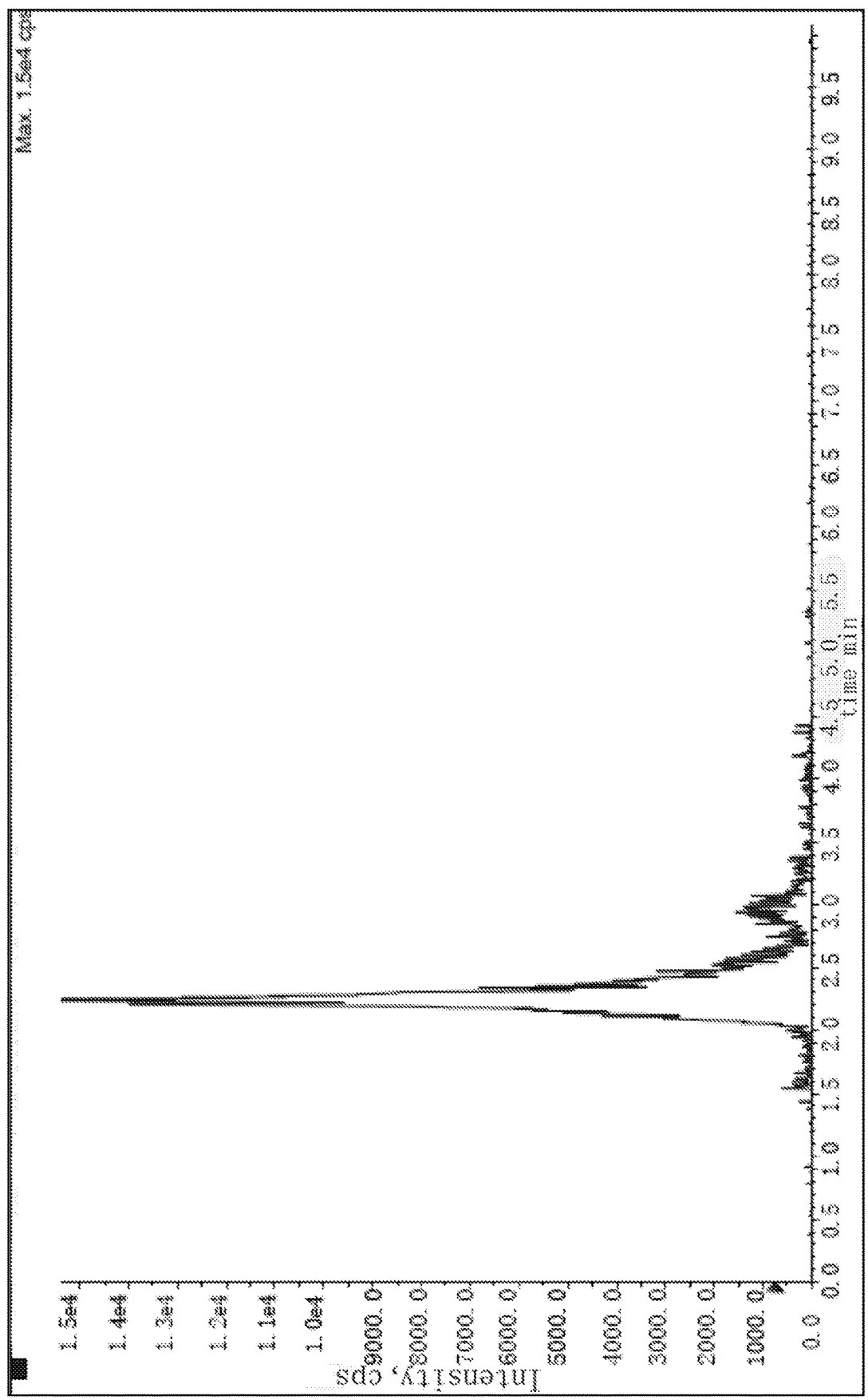
FIG. 9 is a limit of quantification spectrum of the venom sample solution of the *Bothrops atrox* in Embodiment 2.

Database search, screening and determination: National Center of Biotechnology Information (NCBI) and Universal Protein Resource (UniProt) are used to integrate related snake protein library and venom protein library, to establish a snake and venom database. A Peptidemass function provided by Uniprot is used to simulate results of trypsin enzymatic digestion of snake venom-like thrombin proteins from different species, a marker polypeptide sequence of *Bothrops atrox* relative to other species is obtained by aligning a sequence of a *Bothrops atrox*-like thrombin protein with sequences of the other species, and Proteome Discoverer software (version 2.2) is used to search a mass spectrometry data library, referring to the following principles: (1) 8~25 amino acids, (2) trying to avoid an artificially modified peptide fragment, and (3) no missed cut sites during enzyme digestion and other principles. Combined with the mass spectrometry response and separation conditions, it is determined that "EAYNGLPAK (SEQ ID NO: 1)" may be used as the marker polypeptide of the *Bothrops atrox*-like thrombin, and used to characterize the species source and content of the *Bothrops atrox*-like thrombin. The detection results show that the molecular weight and secondary mass spectrometry of the marker polypeptide are consistent with theoretical values, as shown in FIG. 1 and FIG. 2.

Second Embodiment

Multi-reaction monitoring (MRM) qualitatively and quantitatively analyzes a *Bothrops atrox*-like thrombin in a sample.

1. Instrument and device: SCIEX Triple Quad 6500 triple quadrupole mass spectrometer, CP225D electronic balance (Sartorius, Germany), Sigma3-30K refrigerated centrifuge (Sigma, Germany), and Millipore Milli-QAdvantageA10 ultrapure water instrument (Millipore, USA).

2. Chromatography and mass spectrometry condition:

(1) Liquid phase condition: Thermo Hypersil GOLD C18 column (100 mm×2.1 mm, 3 μm); column temperature: 40° C.; injection volume: 10 μL; flow rate: 0.3 mL/min; a mobile phase A is 0.1% formic acid solution, B is 0.1% formic acid acetonitrile, and gradient elution is performed, elution program: 0 to 2 min, mobile phase A 90%; 2 to 6 min, mobile phase A 90% to 60%; 6.1 to 8 min, mobile phase A 30%; and 8.1 to 10 min, mobile phase A 90%.

(2) Mass spectrometry condition: an electrospray ion source, a positive ion scanning mode, multi-reaction monitoring; a mass-to-charge ratio (m/z) double-charge 481.9 to 315.2 is used as a quantitative ion pair, a mass-to-charge ratio (m/z) double-charge 481.9 to 485.2 is used as a qualitative ion pair; the vortex ion spray temperature is 500° C.; ionization voltage: 5.5 kV; the collision chamber exit voltage is 10 V; EP is 10 V; CE is 20 V, and DP is 80 V.

3. Preparation of reference substance solution:

(1) 10 mg of the marker polypeptide (EAYNGLPAK (SEQ ID NO: 1)) screened in the first embodiment is precisely weighed, it is placed in a volumetric flask with a volume of 100 mL, the reference substance is dissolved with ammonium bicarbonate solution with a concentration of 25 mmol/L and the volume is fixed to 100 mL, it is shaken uniformly, to obtain solution b.

(2) 1 mL of the solution b is precisely measured, placed in the volumetric flask with the volume of 100 mL, and then the ammonium bicarbonate solution with the concentration of 25 mmol/L is added and the volume is fixed to 100 mL, it is shaken uniformly, to obtain solution c.

(3) 10 mL of the solution c is precisely measured, placed in the volumetric flask with the volume of 100 mL, and then the ammonium bicarbonate solution with the concentration of 25 mmol/L is added and the volume is fixed to 100 mL, it is shaken uniformly, to obtain 100 ng/mL of marker polypeptide reference substance stock solution.

(4) 0.25 mL, 0.5 mL, 0.8 mL, 1 mL, 1.2 mL, 2 mL, and 3 mL of the marker polypeptide reference substance stock solution prepared in the step (3) are precisely measured, and then placed in the volumetric flask with the volume of 10 mL respectively, and 25 mmol/L of the ammonium bicarbonate solution is respectively added and the volume is fixed to 10 mL, it is shaken uniformly, to respectively obtain series concentration reference substance solution with concentrations of 2.5 ng/mL, 5 ng/mL, 8 ng/mL, 10 ng/mL, 12 ng/mL, 20 ng/mL, and 30 ng/mL for future use.

4. Preparation of test substance solution: 20 mg of the sample to be detected is taken, and placed in the volumetric flask with the volume of 100 mL, and then the ammonium bicarbonate solution with the concentration of 25 mmol/L is added and the volume is fixed to 100 mL, it is shaken uniformly, to obtain solution d; and 1 mL of the solution d is precisely measured, 10 μL of trypsin solution (newly prepared for immediate use) with a concentration of 10 mg/mL is added, reacted at 37° C. for 4 hours, and a supernatant is taken as test substance solution by centrifugation.

5. Preparation of blank solution: 1 mL of the ammonium bicarbonate solution with the concentration of 25 mmol/L is precisely measured, and 10 μL of 10 mg/mL trypsin solution (newly prepared for immediate use) is added, and reacted at 37° C. for 4 hours, to obtain blank solution for future use.

6. Calculation of thrombin-like content in sample to be detected: 10 μL of the above test substance solution and blank solution are taken, detection is performed according to the chromatography and mass spectrometry conditions in item 2 of this embodiment, the concentration of the marker polypeptide in the reference substance series standard solution is used as an abscissa, the corresponding peak area is used as an ordinate, a linear regression equation is calculated, r>0.99, the concentration of the test substance solution is calculated from the regression equation, and then the thrombin-like content in the sample to be detected is calculated.

7. Specificity investigation: 10 μL of the test substance solution, the blank solution and the reference substance solution are each taken, liquid quality analysis is performed, and integrals are shown in FIG. 3 to FIG. 6 respectively. Results show that the blank solution does not have an interference peak at a peak position of the reference substance solution, and the test substance solution has a response chromatographic peak at the peak position of the reference substance solution, it is indicated that the method has the good specificity.

8. Detection limit and limit of quantification: two parts of the reference substance solution with a concentration of 10 ng/mL are taken, and diluted with the ammonium bicarbonate solution with the concentration of 25 mmol/L, to respectively prepare the reference substance solution with the concentrations of 0.5 ng/mL and 1.25 ng/mL. 10 μL of the reference substance solution is taken respectively, and a high performance liquid chromatography-mass spectrometer is used to detect by using a mass-to-charge ratio (m/z) double-charge 481.9 to 315.2 as a quantitative ion pair, results are shown in FIG. 8 and FIG. 9. It may be seen that the signal-to-noise ratio of the quantitative ion pair of the marker polypeptide is 4.5 while the reference substance solution concentration is 0.5 ng/mL, and the signal-to-noise ratio is 17.4 while the concentration is 1.25 ng/mL, so the detection limit is 0.5 ng/mL, and the limit of quantification is 1.25 ng/mL.

9. Linearity and range: the above prepared series concentration reference substance solution with concentrations of 2.5 ng/mL, 5 ng/mL, 8 ng/mL, 10 ng/mL, 12 ng/mL, 20 ng/mL, and 30 ng/mL is used to detect by using a mass-to-charge ratio (m/z) 481.9 to 315.2 as a quantitative ion pair. The concentration of the marker polypeptide in the reference substance series standard solution is used as an abscissa, the corresponding peak area is used as an ordinate, and a linear regression equation is calculated: $y=143868x-54779$ ($R^2=0.9992$), and within a range of 2.5 ng/mL~30 ng/mL, the concentration of the marker polypeptide has a linear relationship with the chromatographic peak area, and results are shown in FIG. 9.

10. Repeatability: according to a preparation method for the test substance (snake venom sample batch number of *Bothrops atrox:* 180411) solution, 6 copies are prepared in parallel and then analyzed, detection is performed by using a mass-to-charge ratio (m/z) double-charge 481.9 to 315.2 as a quantitative ion pair. Results are shown in Table 1, and it may be seen that: relative standard deviation (RSD) of the contents measured in parallel for six times is 3.3%, it is indicated that the test method has the good repeatability.

TABLE 1

| Number | Injection volume (mg) | Concentration (ng/mL) | Content (ng/mg) |
|---|---|---|---|
| 1 | 20.21 | 20.07 | 99.31 |
| 2 | 20.37 | 20.63 | 101.27 |
| 3 | 19.85 | 20.56 | 103.57 |
| 4 | 20.51 | 20.63 | 100.58 |
| 5 | 20.05 | 20.35 | 101.49 |
| 6 | 19.98 | 21.75 | 108.85 |
| Mean | / | / | 102.51 |
| RSD | / | / | 3.3% |

11. Precision investigation: the test substance (snake venom sample batch number of *Bothrops atrox:* 180411) solution is taken, sample injection is continuously repeated for 6 times, and a mass-to-charge ratio (m/z) double-charge 481.9 to 315.2 is used as a quantitative ion pair, to measure the peak area, results are shown in Table 2, and it may be seen that: RSD is 2.3%, it is indicated that the instrument precision is good.

TABLE 2

| Number | Peak area | Mean | RSD (%) |
|---|---|---|---|
| 1 | 1.46E+06 | 1.43E+06 | 2.3 |
| 2 | 1.44E+06 | | |
| 3 | 1.39E+06 | | |
| 4 | 1.42E+06 | | |
| 5 | 1.40E+06 | | |
| 6 | 1.47E+06 | | |

12. Stability investigation: the test substance (snake venom sample batch number of *Bothrops atrox:* 180411) solution is taken, placed at 8° C. after treatment, and samples are injected and measured respectively at 0, 2, 4, 6, 8, 16 and 24 hours, and a mass-to-charge ratio (m/z) double-charge 481.9 to 315.2 is used as a quantitative ion pair. Results are shown in Table 3, and it may be seen that RSD of the measured peak area is 2.6%, it is indicated that the marker polypeptide in the test substance solution is stable at 8° C. within 24 hours.

TABLE 3

| Time (h) | Peak area | Mean | RSD (%) |
|---|---|---|---|
| 0 | 2.87E+06 | 2.92E+06 | 2.6 |
| 2 | 2.91E+06 | | |
| 4 | 2.90E+06 | | |
| 6 | 2.79E+06 | | |
| 8 | 2.95E+06 | | |
| 16 | 2.99E+06 | | |
| 24 | 3.02E+06 | | |

13. Investigation of recovery rate: 21.78 mg of a snake venom sample with the known marker polypeptide content (snake venom sample batch number of *Bothrops atrox:* 180411, the marker polypeptide content: 102.51 ng/mg) is precisely weighed, and dissolved with 10 ng/mL of marker polypeptide reference substance solution (dissolved with the ammonium bicarbonate aqueous solution with the concentration of 25 mmol/L) and diluted to 100 mL. Then 6 parts of the obtained solution are taken, each part is 1 mL, an appropriate amount of the marker polypeptide reference substance solution is added to each part, recovery rate investigation solution is prepared according to the preparation in item 4 of this embodiment, and a mass-to-charge ratio (m/z) double-charge 481.9 to 315.2 is used as a quantitative ion pair to detect. Results are shown in Table 4, and it may be seen that: the recovery rates of three levels are all in the range of 95.1%~106.1%, the average recovery rate is 99.2%, and RSD is 4.5%. The recovery rate of this method is good.

TABLE 4

| Number | Content in sample (ng) | Addition amount (ng) | Measured value (ng) | Recovery rate (%) | Average recovery rate (%) | RSD (%) |
|---|---|---|---|---|---|---|
| 1 | 2233 | 1000 | 3210 | 97.7 | 99.2 | 4.5 |
| 2 | | | 3189 | 95.6 | | |
| 3 | | | 3294 | 106.1 | | |
| 4 | | | 3184 | 95.1 | | |
| 5 | | | 3266 | 103.3 | | |
| 6 | | | 3208 | 97.5 | | |

14. Sample detection: according to the methods in items 3~6 of this embodiment, the samples marked as the venom of the *Bothrops atrox* (180411, 201208, 200723), three batches of venom samples of the *Agkistrodon halys ussuriensis* (20180601F, 20180702F, 20170802) and two batches of venom samples of unknown snake species (20200304, 20200405) are detected.

14.1. Qualitative analysis: according to the snake venom sample pre-treatment method and analysis method described above, test results show that in a test substance ion chromatogram extracted by using the mass-to-charge ratio (m/z) double-charge 481.9 to 315.2 and the mass-to-charge ratio (m/z) double-charge 481.9 to 485.2 as the ion pairs, the three batches of the *Bothrops atrox* venom samples show the chromatographic peaks consistent with the chromatographic retention time (2.25 minutes) of the control marker polypeptide, while the three batches of the *Agkistrodon halys ussuriensis* venom samples (20180601F, 20180702F, 20170802) and two batches of the snake venom samples with the unknown snake species (20200304, 20200405) do not extract the chromatographic peaks at the chromatographic retention time of the control marker polypeptide. Therefore, the marker polypeptide EAYNGLPAK (SEQ ID NO: 1) may be detected in the three batches of the snake venom marked as the *Bothrops atrox*, it is confirmed that it comes from the *Bothrops atrox*, while the other five batches of the snake venom do not detect the marker polypeptide, which is not a source of the *Bothrops atrox*.

14.2. Quantitative analysis: for the samples in which the marker polypeptide (EAYNGLPAK (SEQ ID NO: 1)) is detected, the concentration of the test substance solution is calculated from the regression equation, and then the content of the thrombin-like marker polypeptide in the sample is calculated. Results are shown in Table 5, and it may be seen that the contents of the marker polypeptides in the three batches of crude venom are all above 100 ng/mg, so this method may be used to detect the content of the thrombin-like enzyme in the snake venom of the *Bothrops atrox* in the sample.

TABLE 5

| Batch number | Content (ng/mg) |
| --- | --- |
| 180411 | 102.51 |
| 201208 | 110.9 |
| 200723 | 105.4 |

The above only illustrate several implementation modes of the present disclosure, and should not be understood as limiting a patent scope of the present disclosure. It should be pointed out that for other persons in the art, without departing from the spirit and scope of the present disclosure, modifications, replacements, improvements and the like may be made, and these all belong to a scope of protection of the present disclosure. Therefore, the scope of patent protection of the present disclosure should be based on the descriptions according to the claims.

SEQUENCE LISTING

```
Sequence total quantity: 1
SEQ ID NO: 1             moltype = AA  length = 9
FEATURE                  Location/Qualifiers
source                   1..9
                         mol_type = protein
                         organism = Bothrops atrox
SEQUENCE: 1
EAYNGLPAK                                                                 9
```

What is claimed is:

1. A marker polypeptide of a *Bothrops atrox*-like thrombin, wherein its amino acid sequence is EAYNGLPAK (SEQ ID NO: 1).

2. A method for detecting a species source of a snake venom-like thrombin, wherein the following steps are used:
   (1) adding a trypsin to a sample to be detected to perform enzymolysis pre-treatment, and taking a supernatant; a specific operation is as follows: taking 20 mg of the sample to be detected, and then adding an ammonium bicarbonate solution with a concentration of 25 mmol/L and fixing the volume to 100 mL, and shaking uniformly, to obtain a solution; measuring 1 mL of the solution, adding 10 μL of a trypsin solution with a concentration of 10 mg/mL, reacting at 37° C. for 4 hours, and taking the supernatant by centrifugation;
   (2) injecting the supernatant into a liquid chromatography-mass spectrometer respectively, using an electrospray positive ion mode to perform a multi-reaction monitoring, using a mass-to-charge ratio double-charge of 481.9 to 485.2 as a qualitative ion pair, and using a mass-to-charge ratio double-charge of 481.9 to 315.2 as a quantitative ion pair, to detect the supernatant;
   in detection conditions of a liquid phase and a mass spectrometry in the liquid chromatography-mass spectrometer, the liquid phase conditions are: Thermo Hypersil GOLD C18 chromatographic column (100 mm×2.1 mm, 3 μm); column temperature: 40° C.; injection volume: 10 μL; flow rate: 0.3 mL/min; a mobile phase A is 0.1% of a formic acid solution, B is 0.1% of a formic acid acetonitrile, and gradient elution is performed, elution program: 0 to 2 min, mobile phase A 90%; 2 to 6 min, mobile phase A 90% to 60%; 6.1 to 8 min, mobile phase A 30%; and 8.1 to 10 min, mobile phase A 90%;
   in the detection conditions of the liquid phase and the mass spectrometry in the liquid chromatography-mass spectrometer, the mass spectrometry conditions are: an electrospray ion source, a positive ion scanning mode, and the multi-reaction monitoring; a vortex ion spray temperature is 500° C.; an ionization voltage is 5.5 kV; a collision chamber exit potential is 10 V; an entry potential is 10 V; a collision energy is 20 V, and a declustering potential is 80 V;
   (3) if a chromatogram obtained in the step (2) shows a chromatographic peak consistent with a retention time of a control marker polypeptide chromatogram, it is indicated that the sample to be detected is from *Bothrops atrox*; and otherwise, it is not a source of the *Bothrops atrox*, wherein an amino acid sequence of the control marker polypeptide is EAYNGLPAK (SEQ ID NO: 1).

3. A method for detecting a content of a snake venom-like thrombin, wherein the following steps are used:
   (i) taking a marker polypeptide of a *Bothrops atrox*-like thrombin, dissolving and diluting to prepare a series concentration of reference substance solution, wherein an amino acid sequence of the marker polypeptide is EAYNGLPAK (SEQ ID NO: 1);

(ii) using the sample derived from the *Bothrops atrox* detected in the method for detecting the species source of the snake venom-like thrombin according to claim 2 as an object to be detected, and adding a trypsin to the object to be detected to perform enzymolysis pretreatment, wherein a specific operation is as follows: taking 20 mg of the sample to be detected, and then adding an ammonium bicarbonate solution with a concentration of 25 mmol/L and fixing the volume to 100 mL, and shaking uniformly, to obtain a solution; measuring 1 mL of the solution, adding 10 µL of a trypsin solution with a concentration of 10 mg/mL, reacting at 37° C. for 4 hours, and taking a supernatant as a test substance solution by centrifugation; injecting the test substance solution into a liquid chromatography-mass spectrometer, using an electrospray positive ion mode to perform a multi-reaction monitoring, using a mass-to-charge ratio double-charge of 481.9 to 485.2 as a qualitative ion pair, and using a mass-to-charge ratio double-charge of 481.9 to 315.2 as a quantitative ion pair, to detect the supernatant;

in detection conditions of a liquid phase and a mass spectrometry in the liquid chromatography-mass spectrometer, the liquid phase conditions are: Thermo Hypersil GOLD C18 chromatographic column (100 mm×2.1 mm, 3 µm); column temperature: 40° C.; injection volume: 10 µL; flow rate: 0.3 mL/min; a mobile phase A is 0.1% of a formic acid solution, B is 0.1% of a formic acid acetonitrile, and gradient elution is performed, elution program: 0 to 2 min, mobile phase A 90%; 2 to 6 min, mobile phase A 90% to 60%; 6.1 to 8 min, mobile phase A 30%; and 8.1 to 10 min, mobile phase A 90%;

in the detection conditions of the liquid phase and the mass spectrometry in the liquid chromatography-mass spectrometer, the mass spectrometry conditions are: an electrospray ion source, a positive ion scanning mode, and the multi-reaction monitoring; a vortex ion spray temperature is 500° C.; an ionization voltage is 5.5 kV; a collision chamber exit potential is 10 V; an entry potential is 10 V; a collision energy is 20 V, and a declustering potential is 80 V;

(iii) extracting a chromatogram of which the mass-to-charge ratio double-charge is 481.9 to 315.2, taking a concentration of the marker polypeptide in the series concentration of reference substance solution in the step (i) as an abscissa, taking a peak area corresponding to the chromatogram in the step (ii) as an ordinate, calculating a linear regression equation, calculating a concentration of the test substance solution from the regression equation, and then calculating a thrombin-like content in the object to be detected.

4. The method for detecting the content of the snake venom-like thrombin according to claim 3, wherein in the step (iii), r of the linear regression equation is >0.99.

* * * * *